United States Patent
Akiyama et al.

[11] Patent Number: 5,986,274
[45] Date of Patent: Nov. 16, 1999

[54] CHARGED PARTICLE IRRADIATION APPARATUS AND AN OPERATING METHOD THEREOF

[75] Inventors: Hiroshi Akiyama, Hitachi; Kazuo Hiramoto, Hitachiota; Koji Matsuda; Tetsuo Norimine, both of Hitachi, all of Japan

[73] Assignee: Hitachi, Ltd., Tokyo, Japan

[21] Appl. No.: 09/018,317

[22] Filed: Feb. 3, 1998

[30] Foreign Application Priority Data

Feb. 7, 1997 [JP] Japan ................................. 9-024738
Aug. 19, 1997 [JP] Japan ................................. 9-232111

[51] Int. Cl.$^6$ .............................. A61W 5/00; H01J 33/00
[52] U.S. Cl. ................................. 250/492.3; 350/492.1; 350/492.21; 350/505.1
[58] Field of Search .............. 250/492.3, 492.1, 250/492.21, 505.1, 398; 378/64, 65; 600/2

[56] References Cited

U.S. PATENT DOCUMENTS

| | | | |
|---|---|---|---|
| 4,870,287 | 9/1989 | Cole et al. ............................ | 250/492.3 |
| 5,012,111 | 4/1991 | Ueda .................................... | 250/492.3 |
| 5,440,133 | 8/1995 | Moyers et al. ..................... | 250/492.3 |

FOREIGN PATENT DOCUMENTS 0 754 474 A2   1/1997   European Pat. Off. ......... A61N 5/10

Primary Examiner—Edward P. Westin
Assistant Examiner—Nikita Wells
Attorney, Agent, or Firm—Antonelli, Terry, Stout & Kraus, LLP

[57] ABSTRACT

A charged particle irradiation apparatus, which is capable of decreasing a lateral dose falloff at boundaries of irradiation field of charged particle beam, and reducing the size of the charged particle irradiation apparatus, is provided by controlling magnetic fields of quadrupole electromagnets 1–5 and deflection electromagnets 6–8 so that center of the charged particle beam passes always center of a scatterer irrespective of direction and intensity of a magnetic field generated by scanning electromagnets 50, 60.

10 Claims, 9 Drawing Sheets

(IN DEFLECTION PLANE)

IN A PLANE PERPENDICULAR
TO THE DEFLECTION PLANE

CHARGED PARTICLE IRRADIATION APPARATUS AND AN OPERATING METHOD THEREOF

BACKGROUND OF THE INVENTION

The present invention relates to a charged particle irradiation apparatus for irradiating irradiation targets with charged particles. The charged particle irradiation apparatus is applied for various purposes such as remedies of cancer, sterilization of foods, improved breeding of plants, nondestructive inspection of machine structures, and others.

In accordance with a conventional charged particle irradiation apparatus, a charged particle beam has been enlarged by a scatterer and the like in order to obtain a wide irradiation area, of which dose distribution is uniform. For example, in order to remedy a cancer by irradiation with protons, heavy particles, and the like, it is necessary to enlarge the charged particle beam having an energy of approximately 230 MeV at maximum up to approximately 20 cm in diameter in a case of protons. Then, the enlarged charged particle beam is formed in a shape of the irradiation target, an affected part, by a collimator. Subsequently, the affected part is irradiated with the charged particle beam.

The Japanese Utility Model Publication No. Hei 5-40479 (1993) taught a method that, by employing a Wobbler method of scanning the charged particle beam with two units of deflection magnet, the charged particle beam is enlarged by passing through a scatterer, which is provided in the upstream or the downstream of the two units of deflection magnet.

However, in accordance with the prior art, both the two units of the deflection electromagnet were arranged inside the irradiation apparatus, which had caused a problem of increasing the size of the irradiation apparatus. The increase in size of the irradiation apparatus necessitates a larger rotation radius of the rotation gantry, which makes the whole devices larger, and causes a problem of an increase in construction cost.

The Wobbler method shows a property that the longer the distance between a focus position of the Wobbler's deflection electromagnet and a position of the scatterer gets, the wider the lateral dose falloff (half-shadow blur) of the shape of the charged particle beam formed by the collimator becomes.

SUMMARY OF THE INVENTION

One of the objects of the present invention is to provide a charged particle irradiation apparatus, which is decreased in size by restraining the lateral dose falloff.

One of characteristics of the present invention to achieve the above object is that the charged particle beam passes through a substantially same passing point in the scatterer irrespective of intensity of a magnetic field generated by scanning magnets.

The characteristics leads to the following effects: because the charged particle beam scanned by the scanning magnets passes through the single passing point irrespective of the intensity of the magnetic field generated by the scanning magnets, the passing point can be regarded as a focus position achieved by the scanning magnets. Because the focus position locates near the scatterer, the distance between the focus position and the scatterer position is short, and the lateral dose falloff caused by the scanning magnets can be decreased. The shorter the distance between the focus position and the scatterer position is, the narrower the lateral dose falloff becomes. If the focus position lies within the scatterer, the lateral dose falloff becomes even narrower. If the focus position lies in the center of the scattere's thickness, the lateral dose falloff becomes the minimum. Therefore, an irradiation with a precisely target-shaped charged particle beam becomes possible.

In the above case, if the scanning magnets are arranged in the upstream of the charged particle beam apparatus, the size of the charged particle beam apparatus can be decreased.

Furthermore, if a phase of betatron oscillation of the charged particle beam at the scanning magnets arranged in the upstream of the scatterer differs from the phase of the betatron oscillation of the charged particle beam at the scatterer by approximately 180 degrees or an integral multiple of 180 degrees, the center of the charged particle beam at the scatterer locates at a position corresponding to a node of the betatron oscillation. Therefore, the charged particle beam passes through an approximately same passing point irrespective of the intensity of the magnetic field generated by the scanning magnets, and the lateral dose falloff can be decreased.

One of the other characteristics of the present invention is the arrangement of the scatterer at approximately middle of two scanning magnets, each of which scans the charged particle beam in a same direction. A focus point of the deflection is formed at a middle of two scanning electromagnets by arranging the two scanning electromagnets in parallel each other in a transmitting direction of the charged particle beam. Then, if a scatterer is arranged at the focus point of the deflection formed by the two scanning electromagnets, the charged particle beam passes through always an approximately same passing point in the scatterer. In this case, the charged particle beam passes through the approximately same passing point irrespective of the intensity of the magnetic field generated by the scanning magnets, and the lateral dose falloff can be decreased.

One of the other characteristics of the present invention is in detecting the movement of a target by a movement detector and controlling a supply and a turn-off of the charged particle beam to the charged particle irradiation apparatus by a controller based on the detected movement of the target. In accordance with the above characteristics, the lateral dose falloff can be restrained even when the target moves, and the irradiation with a precisely target-shaped charged particle beam can be performed in correspondence with the movement of the target.

One of the other characteristics of the present invention is in that a compensator fits a range of the charged particle beam into a shape of a lower part of the target, a range shifter changes the energy of the charged particle beam to adjust the range, and a multi-leaf collimator variably modifies the shape of the charged particle beam. In accordance with the above characteristics, the lateral dose falloff can be restrained to an extremely narrow extent even when the target has a complicated three dimensional shape, and the whole target can be irradiated with a charged particle beam being precisely shaped in corresponding to variation in shape of the target.

BRIEF DESCRIPTION OF THE DRAWINGS

The above and further objects and novel feature of the present invention will more fully appear from the following detailed description when the same is read in connection with the accompanying drawings. It is to be expressly understood, however, that the drawings are for purpose of illustration only and are not intended as a definition of the limits of the invention.

DESCRIPTION OF THE PREFERRED EMBODIMENTS

Details of the present invention is explained hereinafter using the preferred embodiments.
(Embodiment 1).

Figure 1:
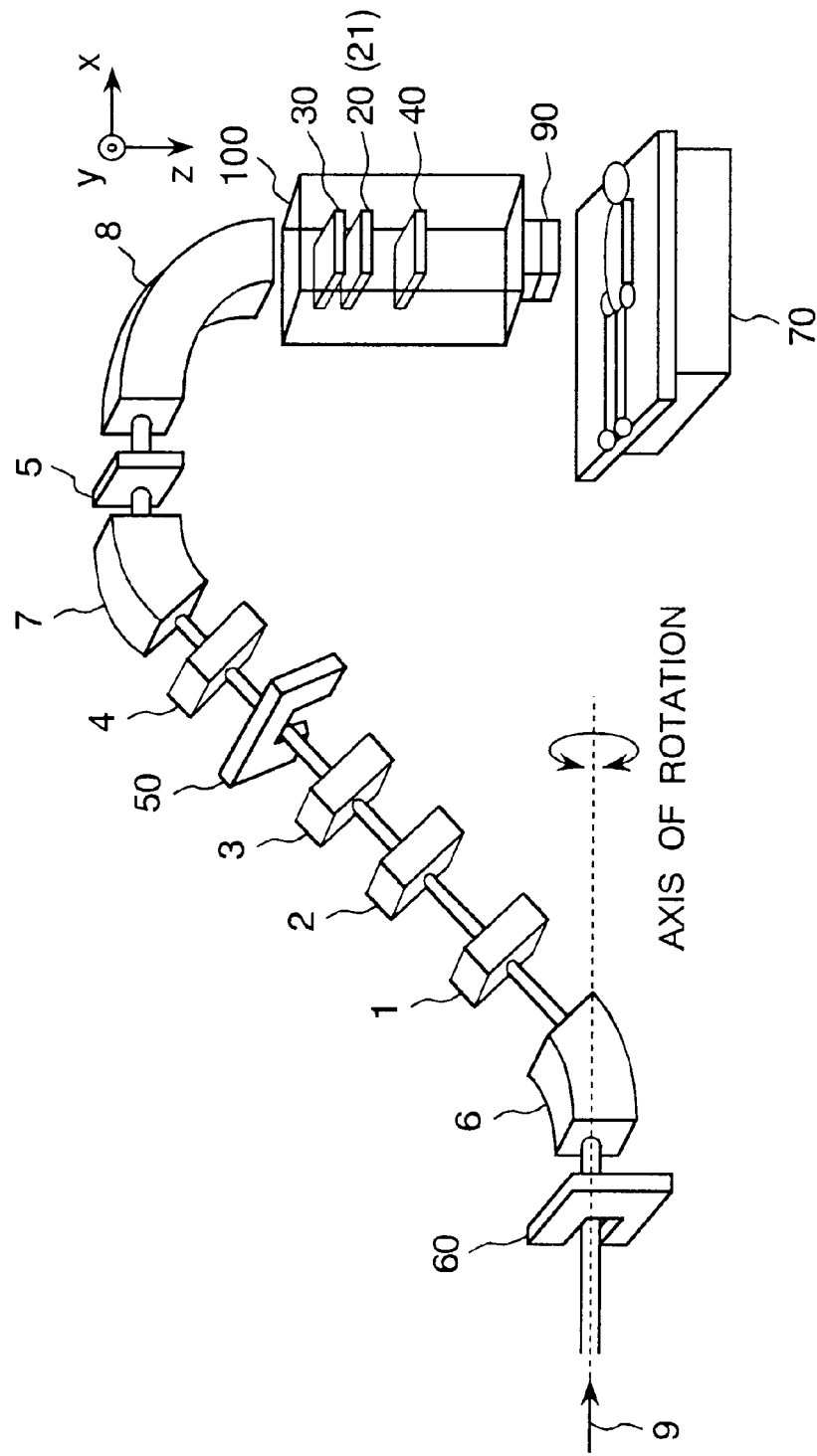
FIG. 1 is a schematic perspective illustration of the charged particle irradiation apparatus according to the first embodiment of the present invention.

The charged particle irradiation apparatus according to the first embodiment of the present invention is indicated in FIG. 1. The charged particle irradiation apparatus of the first embodiment is a rotation type irradiation apparatus which is able to rotate around a bed for patient 70.

A charged particle beam 9 supplied from an accelerator, or the like, is transported using quadrupole 1–5 and deflection electromagnets 6–8 to an irradiation nozzle 100 which is arranged in the downstream of the deflection electromagnet 8. The deflection electromagnets 6–8 deflect the charged particle beam in a same plane (xz plane). Hereinafter, the planes, wherein the deflection electromagnets 6–8 deflect the charged particle beam, are called deflection planes of the deflection electromagnet.

A scanning electromagnet 50 for scanning the charged particle beam is set between the quadrupole electromagnet 3 and the quadrupole electromagnet 4. A scanning electromagnet 60 is arranged in the upstream of the deflection electromagnet 6. The scanning electromagnet 50 generates a magnetic field in a direction (y direction) perpendicular to the deflection plane of the deflection magnet in order to scan the beam in the deflection plane (xz plane) of the deflection magnet. The scanning electromagnet 60 generates a magnetic field in a direction parallel to the deflection plane and perpendicular to the magnetic field (z direction) generated by the scanning electromagnet 50 in order to scan the beam in a direction perpendicular to the deflection plane (y direction) of the deflection magnet.

Figure 2:
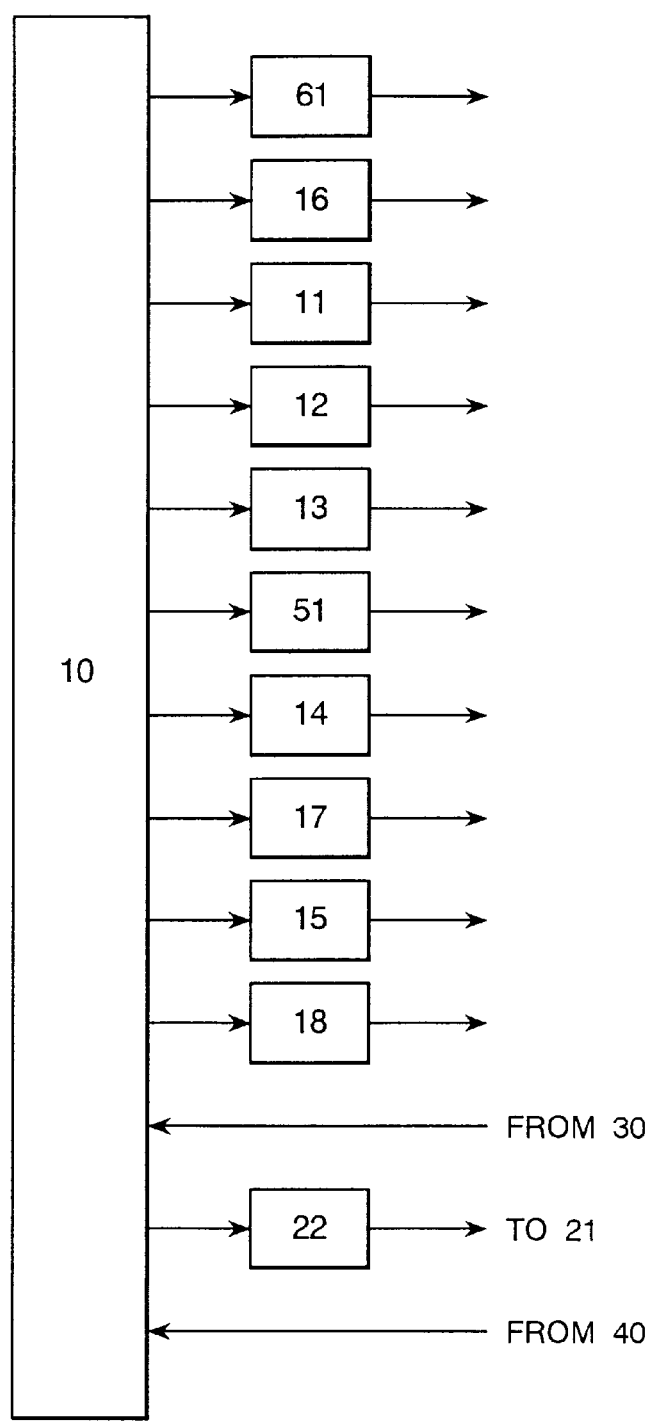
FIG. 2 is a schematic illustration indicating power sources and control devices connected to each of the electromagnets of the charged particle irradiation apparatus according to the first embodiment of the present invention.

The power sources connected to each of the electromagnets are indicated in FIG. 2. Each of the power sources 11–15 for quadrupole electromagnets is connected to each of the quadrupole electromagnets 1–5, respectively. Each of the power sources 16–18 for the deflection electromagnets is connected to each of the deflection electromagnets 6–8, respectively. Each of the power sources 51, 61 is connected to each of the scanning electromagnets 50, 60, respectively. Each of the power sources 11–18, 51, and 61 supplies electric current to each of the quadrupole electromagnets 1–5, each of the deflection electromagnets 6–8, and each of the scanning electromagnets 50 and 60 in accordance with signals from the controller 10, and generates the magnetic field.

The irradiation nozzle 100 is equipped with a beam position monitor 30 for detecting the position of the charged particle beam, a scatterer 20 for scatterering the charged particle beam in order to enlarge the irradiation area, and a profile monitor 40 for detecting the shape of the charged particle beam. The beam position monitor 30 is arranged in the upstream of the scatterer 20, and the profile monitor 40 is set in the downstream of the scatterer 20.

The scatterer is set on a turntable 21. A plurality of the scatterers 20 having different scatterering degrees each from others are set on the turntable 21. The scatterers 20 are interchangeable by operating a turntable driving apparatus 22 based on signals from the controller 10.

The central position of the charged particle beam passing through each of the quadrupole electromagnets, 1–5, the deflection electromagnets 6–8, the scanning electromagnets 50, 60, and the beam position monitor 30 are explained hereinafter.

Figure 3:
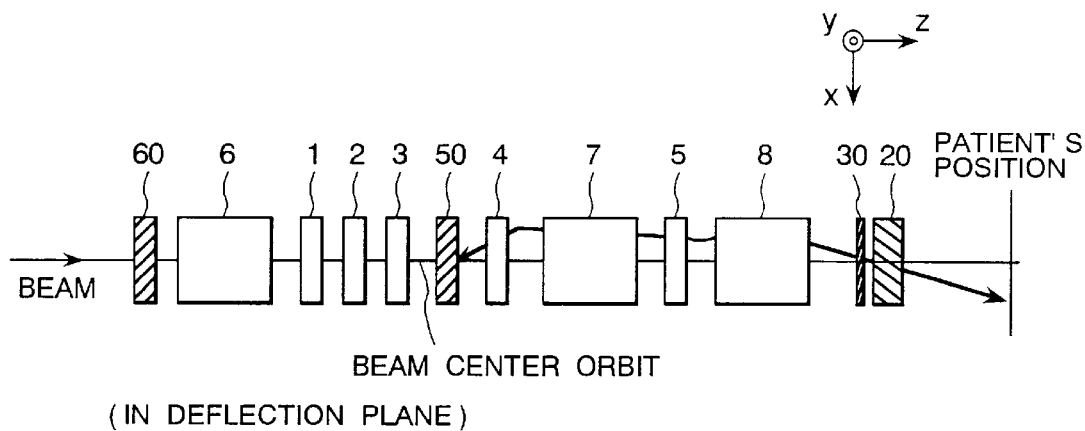
FIG. 3 is a schematic illustration for explaining the center position of the beam on the xz plane of the charged particle irradiation apparatus according to the first embodiment of the present invention.

FIG. 3 indicates schematically the central position of the charged particle beam on the xz plane, that is, the deflection plane of the deflection electromagnet.

When the scanning electromagnet 50 generates a magnetic field in a direction perpendicular to the deflection plane of the deflection electromagnet, that is y direction, the charged particle beam is transmitted with betatron oscillation in the downstream of the scanning electromagnet 50. Accordingly, an orbital gradient of the charged particle beam on the xz plane is varied.

In accordance with the present embodiment, each of the power sources 14, 15, and the power sources 17, 18, for each of the quadrupole electromagnets 4, 5, and the deflection electromagnets 7, 8, arranged in the downstream of the scanning electromagnet 50, are controlled by the controller 10 so that the center of the charged particle beam passes through approximately the center of the scatterer 20. The controls of the power sources 14, 15, and the power sources 17, 18, are performed based on a previously calculated relationship between exciting intensities of respective electromagnets and the central positions of the charged particle beam. Otherwise, the power sources 11–18 can also be controlled based on the central position of the charged particle beam, which has been measured by the beam position monitor 30.

Since the center of the charged particle beampasses through the central position of the scatterer 20, the phase difference in the betatron oscillation of the charged particle beam between the scanning electromagnet 50 and the scatterer 20 is approximately 180 degrees, or an integral multiple of 180 degrees. If the center of the charged particle beam is maintained to pass approximately the central position of the scatterer 20 with the magnetic field generated by the quadrupole electromagnets 4, 5, and the deflection electromagnets 7, 8, the scanning electromagnet 50 and the scatterer 20 are located at positions corresponding to "nodes" in the betatron oscillation of the charged particle beam. Accordingly, the center of the charged particle beam always passes through the central position of the scatterer 20 irrespective of direction and intensity of the magnetic field generated by the scanning electromagnet 50.

Figure 4:
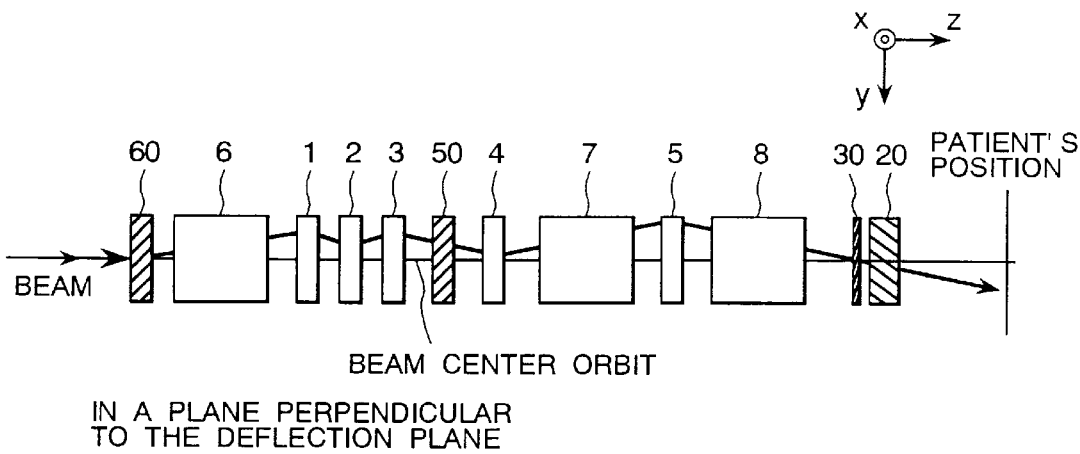
FIG. 4 is a schematic illustration for explaining the center position of the beam on the yz plane of the charged particle irradiation apparatus according to the first embodiment of the present invention.

FIG. 4 indicates schematically the central position of the charged particle beam on a plane perpendicular to the deflection plane of the deflection electromagnet, that is, on the yz plane.

When the scanning electromagnet 60 generates a magnetic field which is in parallel to the deflection plane and perpendicular to the magnetic field generated by the scanning electromagnet 50, the charged particle beam is transmitted with the betatron oscillation perpendicular to the deflection plane in the downstream of the scanning electromagnet 60.

As same as the case of deflection plane of the deflection electromagnet explained previously, the magnetic fields of the quadrupole electromagnets 1–5 and the deflection electromagnets 6–8 are controlled so that the center of the charged particle beam always passes through the central position of the scatterer 20 irrespective of direction and intensity of the magnetic field generated by the scanning electromagnet 60.

The direction of the beam scanning at the patient position is determined by the phase difference in the betatron oscillation between the electromagnets for charged particle beam scanning and the patient position. In the present embodiment, the phase differences in the betatron oscillation between the respective of the scanning electromagnets 50, 60 and the scatterer 20 are both 180 degrees, and the charged particle beam passing through the scatterer 20 is transmitted linearly to the patient position. Therefore, the direction of the scanning at the patient position is opposite to the direction whereto the orbital gradient of the charged particle beam is changed by the scanning electromagnets 50 and 60.

In accordance with the present embodiment, the power sources 51, 61 are controlled so that the current is supplied to the coils of the scanning electromagnets 50, 60 as sinusoidal wave with approximately 90 degrees in the phase difference. The amplitude of the current is controlled so that each of the maximum values in the orbital gradient of the charged particle beam at the scatterer 20 of the respective of the scanning electromagnets becomes equal each other. When the above described current is supplied to the scanning electromagnets 50 and 60, the center of the charged particle beam draws a circular arc at the patient position.

The control of the power sources 51, 61, is performed based on a relationship between the exciting intensities of the respective electromagnets and a shape drawn by the center of the charged particle beam, which has been previously calculated. Otherwise, the power sources 11–18 can also be controlled based on the shape drawn by the center of the charged particle beam, which has been measured by the beam profile monitor 40.

Figure 5:
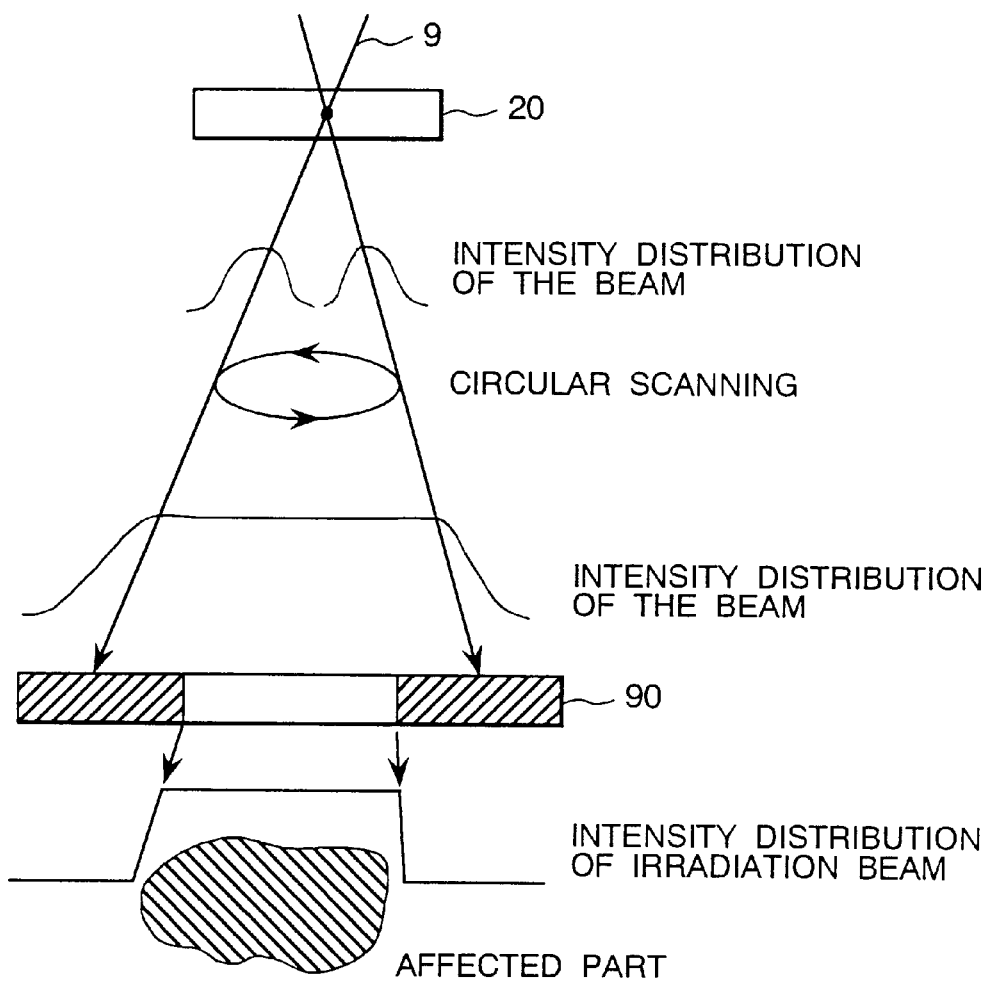
FIG. 5 is a schematic illustration indicating abeam intensity distribution of the charged particle irradiation apparatus according to the first embodiment of the present invention.

The intensity distribution of the charged particle beam irradiated by the charged particle irradiation apparatus relating to the present invention is explained hereinafter referring to FIG. 5.

The intensity of the charged particle beam passed through the scatterer 20 has a Gaussian distribution.

When the charged particle beam is scanned into a circular shape with the scanning electromagnets 50, 60, the intensity of the charged particle beam becomes uniform over the most of inner area of the circle drawn by the center of the charged particle beam. An area adjusted to the shape of the affected part is cut out from the uniform intensity area by the collimator 90, and the affected part is irradiated with the beam which passes through the cut out area. The collimator 90 can be a multi-leaf collimator which is able to change the irradiation range during a therapy irradiation process.

If the center position of the charged particle beam moves when the charged particle beam passes through the scatterer 20, even when the collimator 90 cut out the area of the uniform intensity charged particle beam in the shape of the affected part, the irradiation dose does not decrease rapidly at the boundary of the affected part, and the lateral dose falloff is generated.

However, in accordance with the present embodiment, because the central position of the charged particle beam passing through the scatterer 20 does not move, the intensity of the charged particle beam decreases stepwise at the boundary of the affected part, and the lateral dose falloff can be decreased.

Furthermore, the size of the charged particle beam apparatus can be decreased, because the electromagnets for beam scanning are arranged in the upstream of the charged particle beam apparatus.

A wider irradiation field is required depending on how wide the affected part is. In order to enlarge the irradiation field, the scatterering is broadened by increasing the thickness of the scatterer, or any other means, and the current in the beam scanning electromagnet is increased. In accordance with the present embodiment, the electromagnets are used for the charged particle beam scanning. However, a rotational magnetic field can be generated by rotating a permanent magnet.

Figure 6:
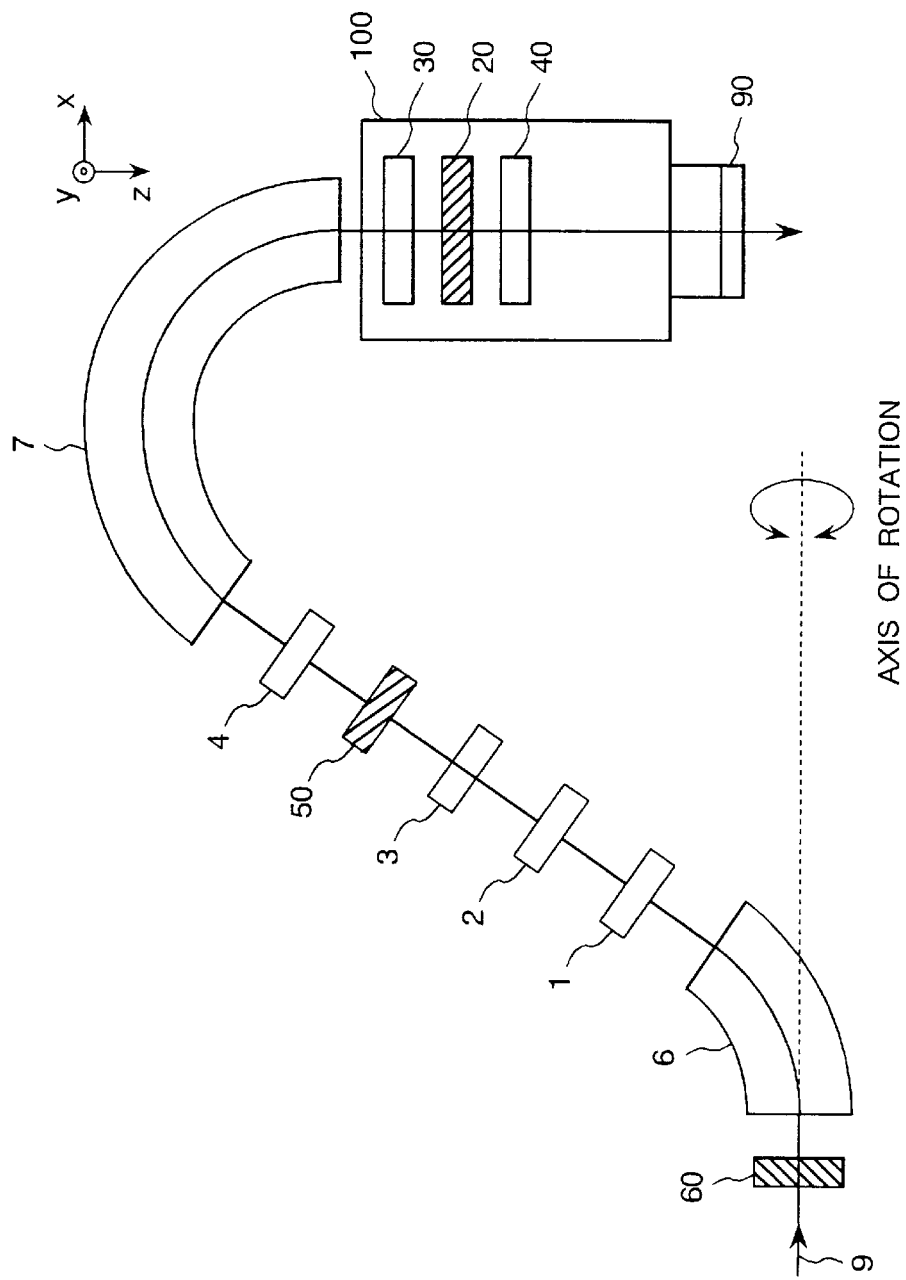
FIG. 6 is a schematic illustration of another charged particle irradiation apparatus according to the first embodiment of the present invention.

Furthermore, as indicatedin FIG. 6, thedeflection magnet is composed of two deflection magnets 6, 7, and the scanning electromagnet 50 can be arranged in the upstream of the deflection electromagnet 7.

In the above explanation, a case when the charged particle beam is scanned in a circular shape was described. However, the same advantages can be achieved even in a case when the beam is scanned linearly, and a case when the beam is irradiated in a standstill, the irradiation position is changed during stopping the irradiation, and the irradiation is resumed after changing the irradiation position.

(Embodiment 2)

Figure 7:
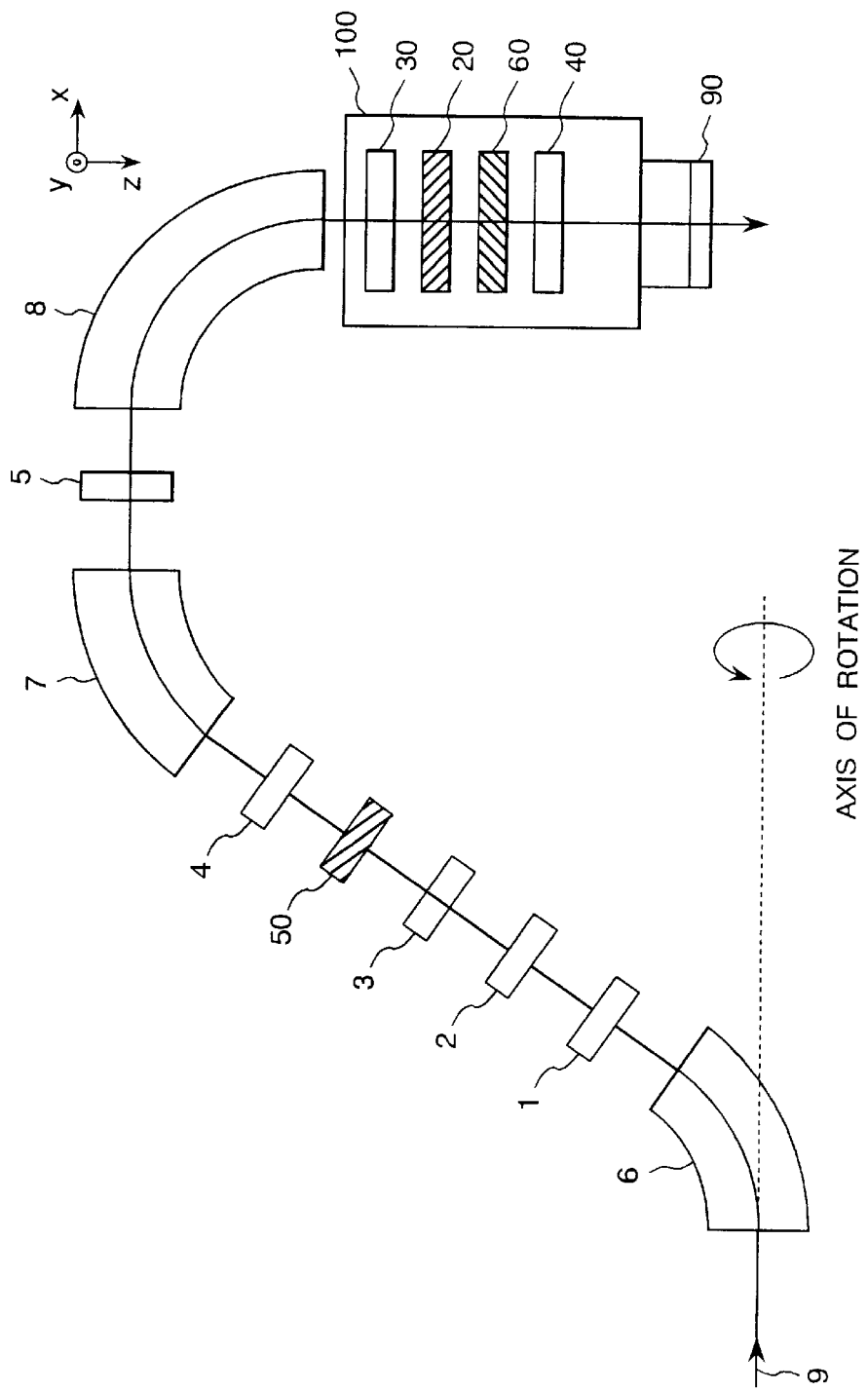
FIG. 7 is a schematic illustration of the charged particle irradiation apparatus according to the second embodiment of the present invention.

The second embodiment of the charged particle irradiation apparatus relating to the present invention is indicated in FIG. 7. In accordance with the first embodiment, the scanning electromagnet 60 was arranged in the upstream of the deflection electromagnet 6. However, in the present embodiment, the scanning electromagnet 60 was arranged in the downstream of the scatterer 20 in the irradiation nozzle 100. As same as the first embodiment 1, the power source 61, which is controlled by the controller 10, is connected to the scanning electromagnet 60 (refer to FIG. 2).

In accordance with the present embodiment, the lateral dose falloff can be decreased because the center of the charged particle beam passes always the center of the scatterer 20 irrespective of direction and intensity of the magnetic field generated by the scanning electromagnet 50, as same as the first embodiment relating to the direction in parallel to the deflection plane of the deflection electromagnet. Furthermore, it is as same as the first embodiment that the controller 10 controls respective of the power sources 14, 15, 17, and 18 of quadrupole electromagnets 4,5, and the deflection electromagnets 7, 8, so that the center of the charged particle beam passes through to 10 approximately the center of the scatterer 20. However, in accordance with the present embodiment, it is not necessary to consider the phase difference of the betatron oscillation between the scanning electromagnet 60 and the scatterer 20. Therefore, the control becomes simpler than the first embodiment.

The scatterer 20 is able to be positioned at downstream side of the scanning electromagnets 50. In the case, it is possible to perform the same effects as above by controlling the power sources 14, 15, 17 and 18 of the quadrapole electromagnets 4,5, and deflection electromagnets 7 and 8 and allowing the center of the charged particle beam to passes through approximately the center of the scatterer 20.

(Embodiment 3)

Figure 8:
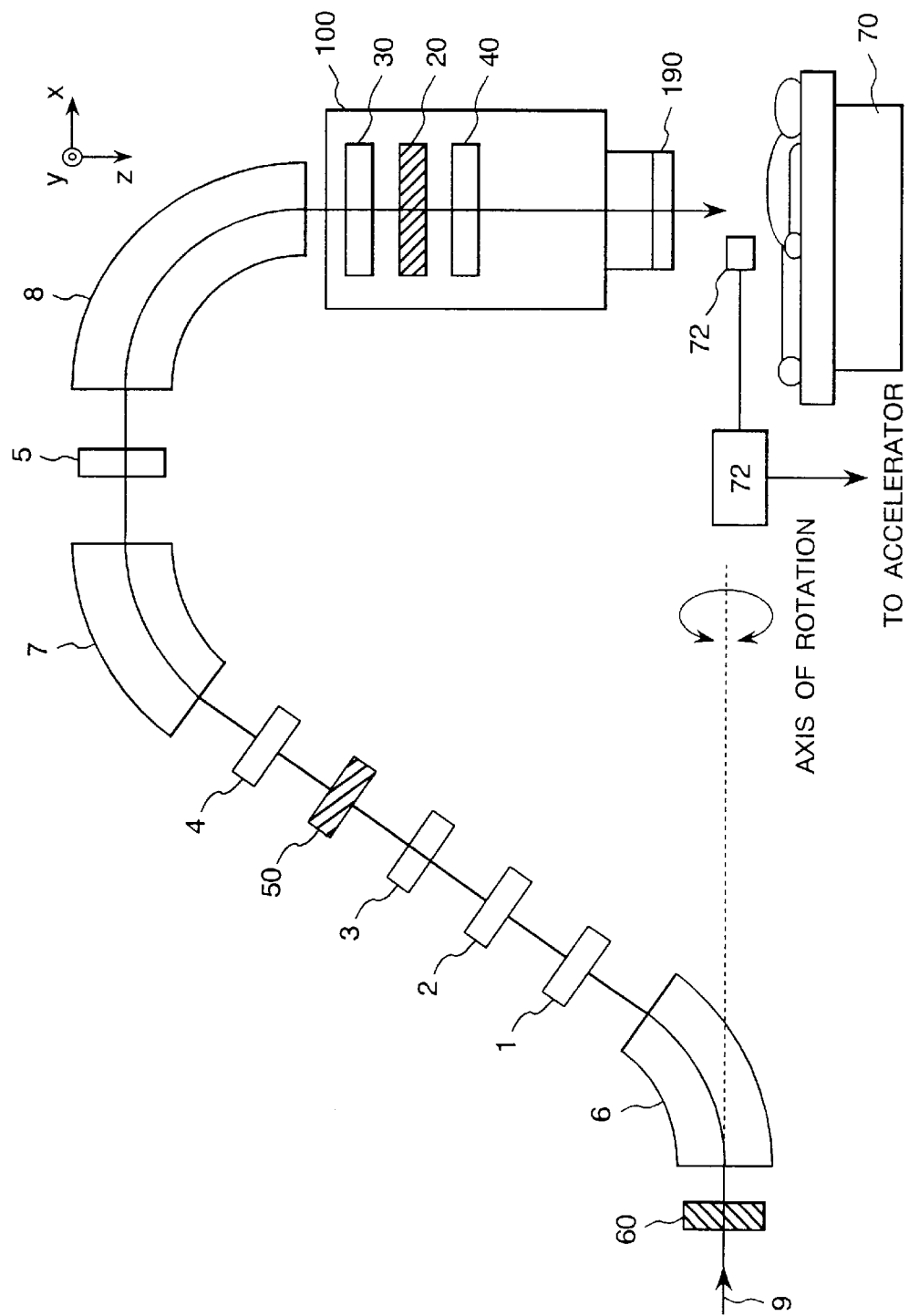
FIG. 8 is a schematic illustration of the charged particle irradiation apparatus according to the third embodiment of the present invention.

The third embodiment of the charged particle irradiation apparatus relating to the present invention is indicated in FIG. 8. The present embodiment uses the charged particle irradiation apparatus of the first embodiment, a breathing sensor 71 for detecting breathing of a patient, and a controller 72 for determining the breathing pattern in accordance with the detected breathing of the patient to control a supply and a turn-off of the charged particle beam to the charged particle irradiation apparatus.

When the patient breathes, an affected part of the patient moves with the breathing. The charged particle irradiation apparatus of the present embodiment performs the irradiation when the affected part is standstill, i.e. when the patient breathes in or breathes out, in accordance with controlling by the controller 72. Therefore, even when the target moves in accordance with breathing, the lateral dose falloff can be restrained to an extremely narrow extent, and the target can be irradiated with a precisely target-shaped charged particle beam.

In the present embodiment, the case when the patient is irradiated with the charged particle beam in synchronization with the breathing of the patient was explained. However, when the target moves, it is possible to control ON or OFF of the irradiation in correspondence with the movement if a means for detecting the movement is used.

(Embodiment 4)

Figure 9:
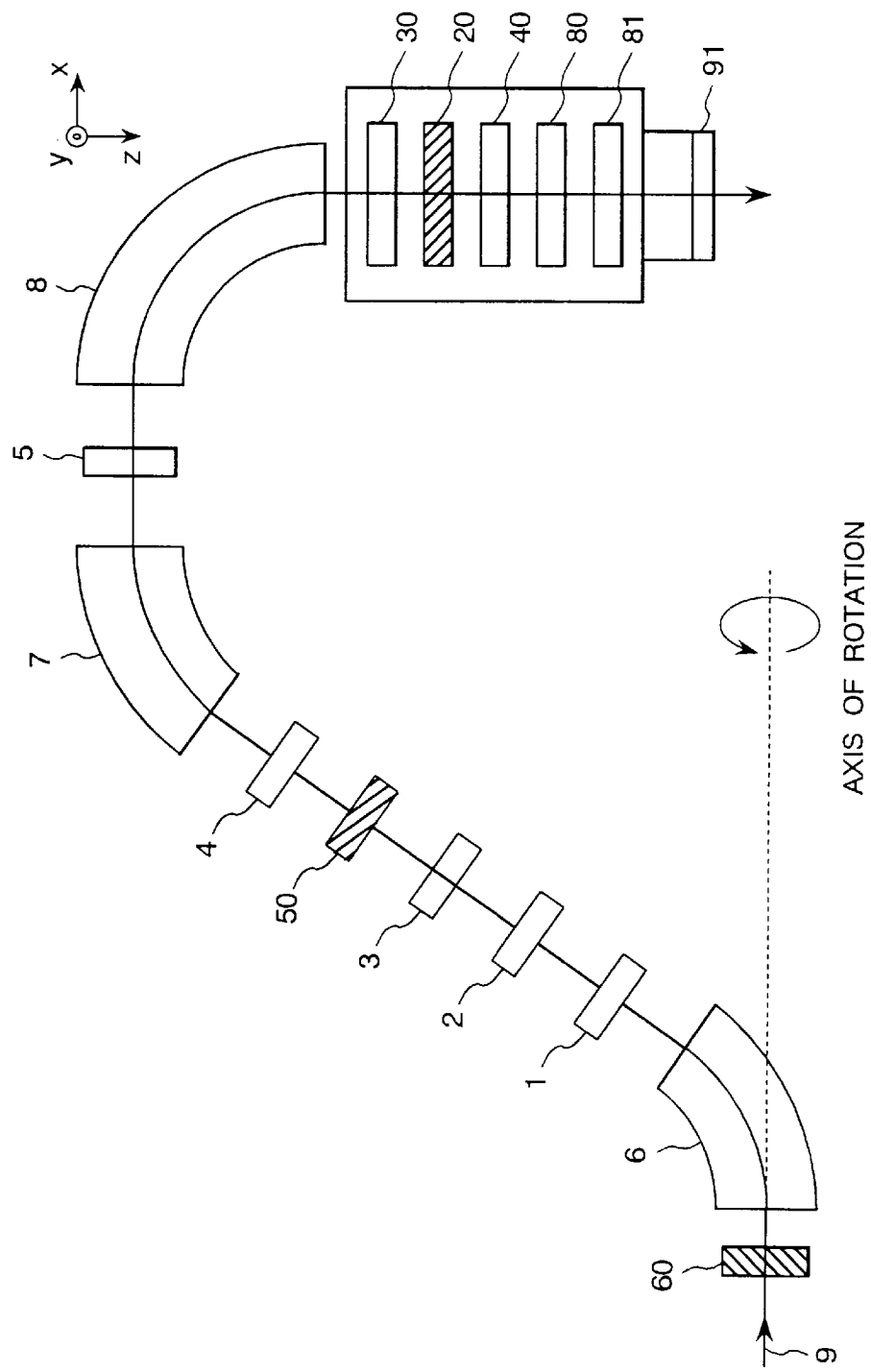
FIG. 9 is a schematic illustration of the charged particle irradiation apparatus according to the fourth embodiment of the present invention.

The fourth embodiment of the charged particle irradiation apparatus relating to the present invention is indicated in FIG. 9. The present embodiment uses the charged particle irradiation apparatus of the first embodiment, a patient compensator 81 for adjusting a range of the charged particle beam to a shape of a lower part of the affected part, and a range shifter (range adjustment device) 80 for changing energy and the range of the charged particle beam. Further, instead of the collimator used in the first embodiment, a multi-leaf collimator 91, which is capable of varying the shape of cutting the chargedparticlebeam, is used. Regularly, the affected part is three-dimensional, and its shape differs depending on the depth.

When scanning with the charged particle beam in the depth direction, the multi-leaf collimator 91 varies the shape, in which the charged particle beam is cut out, corresponding to the variation of the shape. Accordingly, even when the target is a complicated three-dimensional object, the multi-leaf collimator 91 varies its shape, and the lateral dose falloff can be restrained to an extremely narrow extent. Furthermore, the whole target can be irradiated with a precisely target-shaped charged particle beam.

(Embodiment 5)

Figure 10:
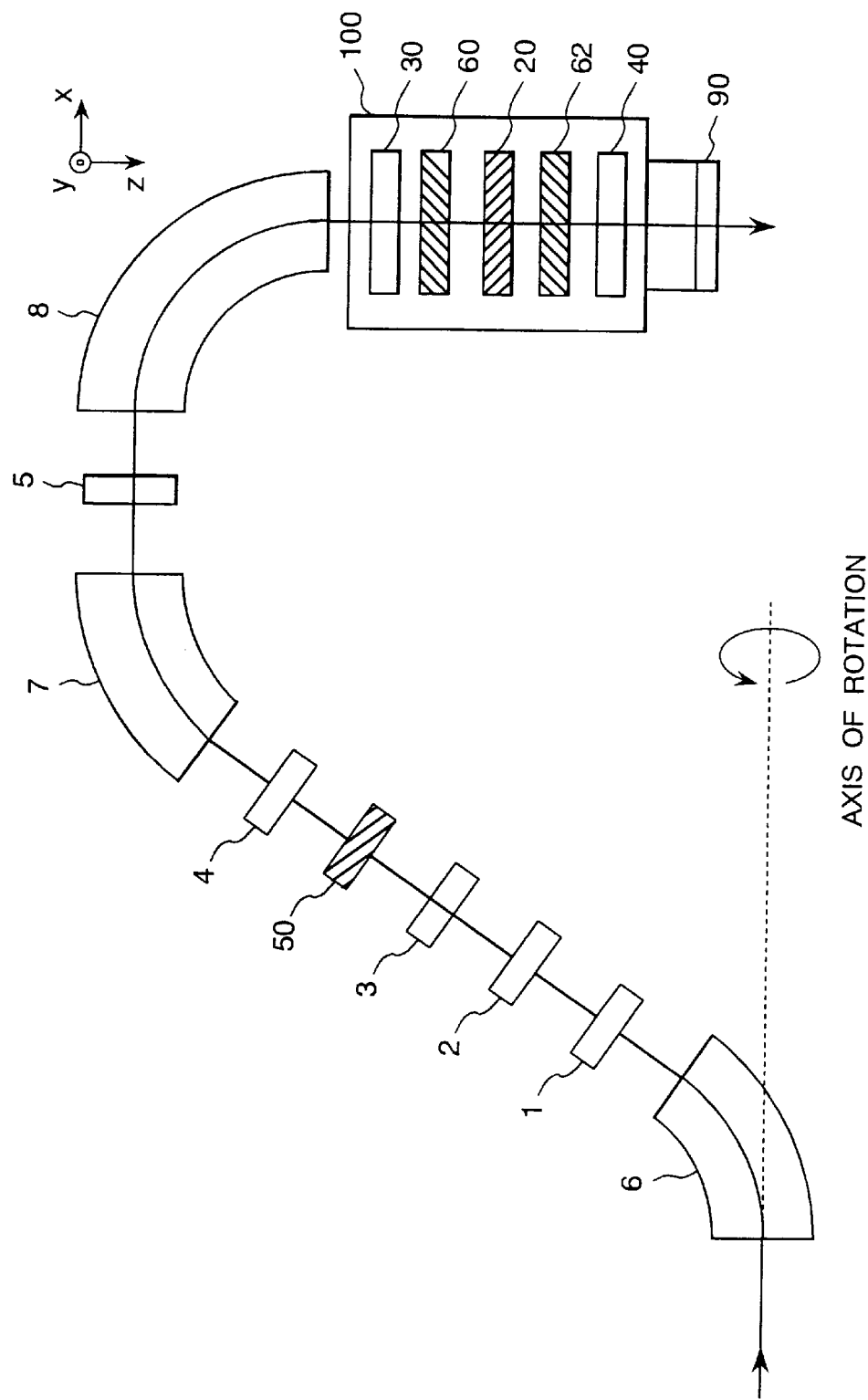
FIG. 10 is a schematic illustration of the charged particle irradiation apparatus according to the fifth embodiment of the present invention.

The fifth embodiment of the charged particle irradiation apparatus relating to the present invention is indicated in FIG. 10. The present embodiment uses two scanning electromagnets 60 and 62. In the first embodiment, the scanning electromagnet 60 for scanning in a direction perpendicular to the deflection plane of the deflection magnet was arranged in the upstream of the deflection electromagnet 6. However, in accordance with the present embodiment, the scanning electromagnets 60, 62 are arranged in the irradiation nozzle 100. The scanning electromagnet 60 is arranged in the upstream of the scatterer 20, and the scanning electromagnet 62 is arranged in the downstream of the scatterer 20. The power source 61 is connected to the scanning electromagnets 60, 62 as same as the first embodiment.

A focus of deflection of the two scanning electromagnets is located at approximately the middle of the respective scanning electromagnets. Therefore, the focus of deflection can be formed at the middle point between the two scanning electromagnets 60, 62 by arranging the two scanning electromagnets 60, 62 in parallel. When the scatterer 20 is placed at the focus position of deflection formedby the two scanning electromagnets 60, 62, the center of the charged particle beam passes always the center of the scatterer 20. Accordingly, the center of the charged particle beam passes always the center of the scatterer 20 irrespective of direction and intensity of the magnetic field generated by the scanning electromagnets 50, 60, and 62, the lateral dose falloff can be decreased as same as the first embodiment.

In the present embodiment, it is as same as the first embodiment that the controller 10 controls respective of the power sources 14, 15, and 17, 18 of quadrupole electromagnets 4,5, and the deflection electromagnets 7, 8, so that the center of the charged particle beam passes through approximately the center of the scatterer 20. However, in accordance with the present embodiment, it is not necessary to consider the phase difference of the betatron oscillation between the scanning electromagnets 60, 62 and the scatterer 20. Therefore, the control becomes simpler than the first embodiment.

In accordance with the present invention, the charged particle beam passes through a substantially same point near the scatterer irrespective of the intensity of the magnetic field. Therefore, since a distance between the focus position formed by the scanning magnet and the scatterer position is small, the lateral dose falloff caused by the scanning magnet can be decreased, and the irradiation can be performed with a precisely target-shaped charged particle beam.

In the above case, if the scanning magnet is arranged in the upstream of the charged particle beam apparatus, the size of the charged particle beam apparatus can be decreased.

Furthermore, in accordance with detecting the movement of a target by a movement detector and controlling a supply and a turn-off of the charged particle beam to the charged particle irradiation apparatus by a controller based on the detected movement of the target, the lateral dose falloff can be restrained even when the target moves, and the irradiation with a precisely target-shaped charged particle beam can be performed in correspondence with the movement of the target.

In accordance with fitting a range of the charged particle beam into a shape of a lower part of the target with a compensator (compensator), adjusting the range by changing the energy of the charged particle beam by a range shifter, and variably modifying the shape of the charged particle beam by a multi-leaf collimator, the lateral dose falloff can be restrained to an extremely narrow extent even when the target has a complicated three dimensional shape, and the whole target can be irradiated with a charged particle beam being precisely shaped in corresponding to variation in shape of the target.

A compensator fits a range of the charged particle beam into a shape of a lower part of the target, a range shifter changes the energy of the charged particle beam to adjust the transmitting range, and a multi-leaf collimator variably modifies the shape of the charged particle beam. In accordance with the characteristics, The lateral dose falloff can be restrained to an extremely narrow extent even when the target has a complicated three dimensional shape, and the whole target can be irradiated with a charged particle beam being precisely shaped in corresponding with variation in shape of the target.

What is claimed is:

1. A charged particle irradiation apparatus comprising:

a scanning magnet for scanning a charged particle beam, a scatterer for scatterering said charged particle beam, and a collimator for making said charged particle beam, which has been scatterered by said scatterer, form a shape of irradiation target, wherein:

said charged particle beam formed by said collimator is irradiated to said irradiation target, further wherein:

said charged particle beam passes through substantially a same point in said scatterer irrespective of an intensity of a magnetic field generated by said scanning magnet.

2. A charged particle irradiation apparatus comprising:

a quadrupole electromagnet, a scanning magnet for scanning a charged particle beam, a scatterer for scatterering said charged particle beam, and a collimator for making said charged particle beam, which has been scatterered by said scatterer, form a shape of irradiation target, wherein:

said charged particle beam formed by said collimator is irradiated to said irradiation target, further comprises:

a controller for controlling an exciting magnitude of said quadrupole electromagnet so that said charged particle beam passes through substantially a same point in said scatterer irrespective of an intensity of a magnetic field generated by said scanning magnet.

3. A charged particle irradiation apparatus comprising:

a scanning magnet for scanning a charged particle beam, a scatterer for scatterering said charged particle beam, which has been scanned by said scanning magnet, and a collimator for making said charged particle beam, which has been scatterered by said scatterer, form a shape of irradiation target, wherein:

said charged particle beam formed by said collimator is irradiated to said irradiation target, further wherein:

a difference between the phase in betatron oscillation of said charged particle beam at said scanning magnet and the phase in betatron oscillation of said charged particle beam at said scatterer is approximately 180 degrees, or approximately an integral multiple of 180 degrees.

4. A charged particle irradiation apparatus comprising:

a quadrupole electromagnet, a scanning magnet for scanning a charged particle beam, a scatterer for scatterering said charged particle beam, which has been scanned by said scanning magnet, and a collimator for making said charged particle beam, which has been scatterered by said scatterer, form a shape of irradiation target, wherein:

said charged particle beam formed by said collimator is irradiated to said irradiation target, further comprises:

a controller for controlling an exciting magnitude of said quadrupole electromagnet so that a difference between the phase in betatron oscillation of said charged particle beam at said scanning magnet and the phase in betatron oscillation of said charged particle beam at said scatterer becomes approximately 180 degrees, or approximately an integral multiple of 180 degrees.

5. A charged particle irradiation apparatus comprising:

a plurality of scanning magnets for scanning a charged particle beam, a scatterer for scatterering said charged particle beam, and a collimator for making said charged particle beam, which has been scatterered by said scatterer, form a shape of irradiation target, wherein:

said charged particle beam formed by said collimator is irradiated to said irradiation target, further wherein:

said scatterer is arranged at approximately middle point between two scanning magnets, which scan the charged particle beam in a same direction, among said plural scanning magnets.

6. A charged particle irradiation apparatus comprising:

a quadrupole magnet, two scanning magnets for scanning a charged particle beam, which has been supplied from an accelerator for accelerating charged particles, in a direction perpendicular to a transmitting direction of said charged particle beam, a scatterer for scatterering said charged particle beam, and a collimator for making said charged particle beam, which has been scatterered by said scatterer, to form a shape of irradiation target, wherein:

said charged particle beam formed by said collimator is irradiated to said irradiation target, further wherein:

said two scanning magnets are mutually perpendicular in a direction to scan said charged particle beam, and at least one of said two scanning magnets is arranged in the stream of said scatterer, further comprises:

a controller for controlling an exciting magnitude of said quadrupole electromagnet so that a difference between the phase in betatron oscillation of said charged particle beam at said scanning magnet, which has been arranged in the upstream of said scatterer, and the phase in betatron oscillation of said charged particle beam at said scatterer becomes approximately 180 degrees, or approximately an integral multiple of 180 degrees.

7. A charged particle irradiation apparatus as claimed in claim 6, further comprises:

a movement detector for detecting movement of said irradiation target, and a supply controller for controlling a supply and a turn-off of the charged particle beam from said accelerator based on the detected movement of the target.

8. A charged particle irradiation apparatus as claimed in claim 6, further comprises:

a compensator for fitting a range of the charged particle beam into a shape of a lower part of the target, and a range shifter for changing the energy of the charged particle beam to adjust the transmitting range, wherein said collimator is a multi-leaf collimator which variably modifies the shape of the charged particle beam.

9. A method for operating a charged particle irradiation apparatus comprising:

a quadrupole electromagnet, a scanning magnet for scanning a charged particle beam, a scatterer for scatterering said charged particle beam, and a collimator for making said charged particle beam, which has been scatterered by said scatterer, to form a shape of irradiation target, wherein:

said charged particle beam formed by said collimator is irradiated to said irradiation target, further wherein:

an exciting magnitude of said quadrupole electromagnet is controlled so that said charged particle beam passes through substantially a same point in said scatterer irrespective of an intensity of a magnetic field generated by said scanning magnet.

10. A method for operating a charged particle irradiation apparatus comprising:

a quadrupole magnet, a scanning magnet for scanning a charged particle beam, a scatterer for scatterering said charged particle beam, and a collimator for making said charged particle beam, which has been scatterered by said scatterer, to form a shape of irradiation target, wherein:

said charged particle beam formed by said collimator is irradiated to said irradiation target, further wherein:

an exciting magnitude of said quadrupole electromagnet is controlled so that a difference between the phase in betatron oscillation of said charged particle beam at said scanning magnet, and the phase in betatron oscillation of said charged particle beam at said scatterer becomes approximately 180 degrees, or approximately an integral multiple of 180 degrees.

* * * * *